US 11,059,490 B1
Jul. 13, 2021

(12) United States Patent
Migneco et al.

(54) SEAT SYSTEM

(71) Applicant: Lear Corporation, Southfield, MI (US)

(72) Inventors: Francesco Migneco, Saline, MI (US); David Gallagher, Sterling Heights, MI (US)

(73) Assignee: Lear Corporation, Southfield, MI (US)

( * ) Notice: Subject to any disclaimer, the term of this patent is extended or adjusted under 35 U.S.C. 154(b) by 0 days.

(21) Appl. No.: 16/821,128

(22) Filed: Mar. 17, 2020

(51) Int. Cl.
| | |
|---|---|
| *B60W 40/08* | (2012.01) |
| *B60N 2/00* | (2006.01) |
| *A61B 5/08* | (2006.01) |
| *A61B 5/00* | (2006.01) |
| *G07C 5/00* | (2006.01) |
| *H04W 4/90* | (2018.01) |
| *G07C 5/08* | (2006.01) |

(52) U.S. Cl.
CPC .......... *B60W 40/08* (2013.01); *A61B 5/0816* (2013.01); *A61B 5/6893* (2013.01); *B60N 2/002* (2013.01); *G07C 5/008* (2013.01); *G07C 5/085* (2013.01); *H04W 4/90* (2018.02); *B60W 2040/0881* (2013.01); *B60W 2540/221* (2020.02)

(58) Field of Classification Search
CPC combination set(s) only.
See application file for complete search history.

(56) References Cited

U.S. PATENT DOCUMENTS

| | | |
|---|---|---|
| 5,769,490 A | 6/1998 | Falzon |
| 6,056,360 A | 5/2000 | Schneider |
| 6,088,642 A | 7/2000 | Finkelstein et al. |
| 6,088,643 A | 7/2000 | Long et al. |
| 6,098,000 A | 8/2000 | Long et al. |
| 6,345,839 B1 | 2/2002 | Kuboki et al. |
| 6,353,207 B1 | 3/2002 | Burt |
| 6,506,153 B1 | 1/2003 | Littek et al. |
| 6,559,422 B2 | 5/2003 | Burt |
| 6,682,494 B1 | 1/2004 | Sleichter, III et al. |
| 6,908,152 B2 | 6/2005 | McMillen |
| 7,011,369 B2 | 3/2006 | Massara et al. |
| 7,083,232 B2 | 8/2006 | Frank |
| 7,083,233 B2 | 8/2006 | Massara et al. |
| 7,152,920 B2 | 12/2006 | Sugiyama et al. |
| 7,201,446 B2 | 4/2007 | Massara et al. |
| 7,219,923 B2 | 5/2007 | Fujita et al. |
| 7,267,652 B2 | 9/2007 | Coyle et al. |
| 7,303,231 B2 | 12/2007 | Frank |
| 7,314,451 B2 | 1/2008 | Halperin et al. |
| 7,417,536 B2 | 8/2008 | Lakshmanan et al. |

(Continued)

FOREIGN PATENT DOCUMENTS

| | | |
|---|---|---|
| CN | 2855822 Y | 1/2007 |
| CN | 203186154 U | 9/2013 |

(Continued)

*Primary Examiner* — Thomas S McCormack

(74) *Attorney, Agent, or Firm* — Fishman Stewart PLLC

(57) ABSTRACT

A seat system includes a seat, a sensor assembly, and/or an electronic control unit (ECU) connected with the sensor assembly. The sensor assembly may be configured to sense a breathing pattern of a user associated with the seat. The ECU may be configured to communicate with a remote server, and at least one of the ECU and the remote server may be configured to determine a medical state of said user according, at least in part, to the breathing pattern.

20 Claims, 6 Drawing Sheets

(56) References Cited

U.S. PATENT DOCUMENTS

| | | | |
|---|---|---|---|
| 7,731,279 B2 | 6/2010 | Asada et al. | |
| 7,808,395 B2 | 10/2010 | Raisanen et al. | |
| 7,862,119 B2 | 1/2011 | Schafer et al. | |
| 7,866,755 B2 | 1/2011 | Okano | |
| 7,900,736 B2 | 3/2011 | Breed | |
| 7,967,379 B2 | 6/2011 | Walters et al. | |
| 7,967,381 B2 | 6/2011 | Sugiyama | |
| 8,341,786 B2 | 1/2013 | Oexman et al. | |
| 8,444,558 B2 | 5/2013 | Young et al. | |
| 8,616,654 B2 | 12/2013 | Zenk et al. | |
| 8,706,204 B2 | 4/2014 | Seo et al. | |
| 8,710,784 B2 | 4/2014 | Meyer et al. | |
| 8,725,311 B1 | 5/2014 | Breed | |
| 8,794,707 B2 | 8/2014 | Bocsanyi et al. | |
| 8,958,955 B2 | 2/2015 | Hotary et al. | |
| 8,971,839 B2 | 3/2015 | Hong | |
| 8,979,191 B2 | 3/2015 | Friderich et al. | |
| 8,989,697 B2 | 3/2015 | Leung et al. | |
| 9,237,242 B2 | 1/2016 | Basir | |
| 9,272,647 B2 | 3/2016 | Gawade et al. | |
| 9,272,689 B2 | 3/2016 | Fung et al. | |
| 9,277,385 B2 | 3/2016 | Iwamoto | |
| 9,427,598 B2 | 8/2016 | Pilla et al. | |
| 9,504,416 B2 | 11/2016 | Young et al. | |
| 9,815,385 B2 | 11/2017 | Lippman et al. | |
| 9,883,821 B2 | 2/2018 | Muehlsteff | |
| 9,978,283 B2 | 5/2018 | Jedrzejewski et al. | |
| 9,980,680 B2 | 5/2018 | Matsumoto | |
| 9,989,571 B2 | 6/2018 | Loftus | |
| 10,034,631 B1 | 7/2018 | Gallagher et al. | |
| 10,210,409 B1 | 2/2019 | Migneco et al. | |
| 10,213,147 B2 | 2/2019 | Gallagher et al. | |
| 10,328,823 B2 | 6/2019 | O'Bannon et al. | |
| 10,358,065 B2 | 7/2019 | McMillen et al. | |
| 10,369,074 B2 | 8/2019 | Oberg et al. | |
| 10,379,535 B2 | 8/2019 | Migneco et al. | |
| 10,391,900 B2 | 8/2019 | Zhao et al. | |
| 10,470,968 B2 | 11/2019 | Saren et al. | |
| 10,471,868 B2 | 11/2019 | Wheeler | |
| 10,492,979 B2 | 12/2019 | Norman et al. | |
| 10,556,532 B2 | 2/2020 | Gallagher et al. | |
| 10,569,668 B2 | 2/2020 | Migneco et al. | |
| 10,576,855 B2 | 3/2020 | Dorfler et al. | |
| 10,640,010 B2 | 5/2020 | Yetukuri et al. | |
| 10,709,386 B2 | 7/2020 | Gallagher et al. | |
| 10,807,439 B2 | 10/2020 | Migneco et al. | |
| 2003/0075959 A1 | 4/2003 | Xue et al. | |
| 2004/0119599 A1 | 6/2004 | Stevenson et al. | |
| 2007/0118054 A1* | 5/2007 | Pinhas | A61B 5/4815 |
| | | | 600/587 |
| 2008/0255731 A1 | 10/2008 | Mita et al. | |
| 2008/0267460 A1 | 10/2008 | Aoki et al. | |
| 2009/0008970 A1 | 1/2009 | Flory et al. | |
| 2009/0030578 A1 | 1/2009 | Periot et al. | |
| 2010/0087748 A1 | 4/2010 | Tobola et al. | |
| 2011/0015468 A1 | 1/2011 | Aarts et al. | |
| 2012/0080911 A1 | 4/2012 | Brykalski et al. | |
| 2012/0086249 A1 | 4/2012 | Rotary et al. | |
| 2013/0090816 A1 | 4/2013 | Huber | |
| 2013/0251216 A1 | 9/2013 | Smowton et al. | |
| 2014/0070943 A1 | 3/2014 | Breed | |
| 2014/0207333 A1 | 7/2014 | Vandivier et al. | |
| 2014/0319895 A1 | 10/2014 | Lange-Mao et al. | |
| 2014/0361871 A1 | 12/2014 | Silva et al. | |
| 2015/0266405 A1 | 9/2015 | Fitzpatrick et al. | |
| 2015/0313475 A1 | 11/2015 | Benson et al. | |
| 2015/0351692 A1 | 12/2015 | Pereny et al. | |
| 2015/0352979 A1 | 12/2015 | O'Bannon et al. | |
| 2015/0352990 A1 | 12/2015 | Zouzal et al. | |
| 2016/0001781 A1* | 1/2016 | Fung | B60W 40/08 |
| | | | 701/36 |
| 2016/0143803 A1 | 5/2016 | Portales | |
| 2016/0250956 A1 | 9/2016 | Setting et al. | |
| 2016/0278709 A1 | 9/2016 | Ridao Granado et al. | |
| 2017/0043681 A1 | 2/2017 | Seiller et al. | |
| 2017/0086588 A1 | 3/2017 | Patrick et al. | |
| 2017/0274906 A1* | 9/2017 | Hassan | B60K 28/14 |
| 2017/0361748 A1 | 12/2017 | Meachum et al. | |
| 2018/0008507 A1 | 1/2018 | Saren et al. | |
| 2018/0009343 A1 | 1/2018 | Saren et al. | |
| 2018/0110960 A1 | 4/2018 | Youngblood et al. | |
| 2018/0325264 A1 | 11/2018 | Gallagher et al. | |
| 2018/0345833 A1 | 12/2018 | Gallagher et al. | |
| 2019/0053761 A1* | 2/2019 | Young | A61B 5/1117 |
| 2019/0054796 A1 | 2/2019 | Thomas | |
| 2019/0126036 A1 | 5/2019 | Franco-Obregon et al. | |
| 2019/0133511 A1 | 5/2019 | Migneco et al. | |
| 2019/0168771 A1 | 6/2019 | Migneco et al. | |
| 2019/0193591 A1 | 6/2019 | Migneco et al. | |
| 2019/0239815 A1 | 8/2019 | Gallagher et al. | |
| 2019/0275860 A1 | 9/2019 | Migneco et al. | |
| 2019/0332902 A1 | 10/2019 | Gallagher et al. | |
| 2019/0337431 A1 | 11/2019 | McMillen et al. | |
| 2019/0344043 A1 | 11/2019 | Migneco et al. | |
| 2020/0035237 A1 | 1/2020 | Kim et al. | |
| 2020/0113344 A1 | 4/2020 | Youngblood et al. | |
| 2020/0170576 A1* | 6/2020 | Lerner | A61B 5/024 |
| 2020/0188211 A1 | 6/2020 | Ellermann | |
| 2020/0231428 A1 | 7/2020 | Migneco et al. | |
| 2020/0253381 A1 | 8/2020 | Dorfler et al. | |

FOREIGN PATENT DOCUMENTS

| | | |
|---|---|---|
| CN | 104252615 A | 12/2014 |
| CN | 205468657 U | 8/2016 |
| DE | 10027686 A1 | 1/2002 |
| DE | 10063478 A1 | 7/2002 |
| DE | 102004010626 A1 | 6/2005 |
| DE | 102004013674 A1 | 10/2005 |
| DE | 102006029871 A1 | 1/2008 |
| DE | 102008029339 A1 | 1/2009 |
| DE | 102009008421 A1 | 10/2009 |
| DE | 102009035566 A1 | 2/2010 |
| DE | 102009031331 A1 | 8/2010 |
| DE | 102009033041 A1 | 1/2011 |
| DE | 102010021332 A1 | 1/2011 |
| DE | 102011012431 A1 | 11/2011 |
| DE | 102011016073 A1 | 12/2011 |
| DE | 102011017238 A1 | 12/2011 |
| DE | 102011102021 A1 | 11/2012 |
| DE | 102011113100 A1 | 3/2013 |
| DE | 102011116194 A1 | 4/2013 |
| DE | 102012201430 A1 | 4/2013 |
| DE | 102012216869 A1 | 3/2014 |
| DE | 202015104103 U1 | 8/2015 |
| DE | 102014002942 A1 | 9/2015 |
| DE | 102015011460 A1 | 3/2016 |
| DE | 102015011461 A1 | 3/2016 |
| DE | 102017110812 A1 | 1/2018 |
| DE | 102016011481 A1 | 3/2018 |
| DE | 202017103162 U1 | 5/2018 |
| DE | 102018000765 A1 | 8/2019 |
| DE | 102018001230 A1 | 8/2019 |
| DE | 202019100400 U1 | 1/2020 |
| DE | 202019100710 U1 | 2/2020 |
| DE | 102018007921 A1 | 4/2020 |
| DE | 202019102879 U1 | 5/2020 |
| DE | 202019105369 U1 | 5/2020 |
| DE | 102019008724 A1 | 8/2020 |
| EP | 1077154 A2 | 2/2001 |
| EP | 1749477 A1 | 2/2007 |
| EP | 1932715 A1 | 6/2008 |
| EP | 2149475 A1 | 2/2010 |
| EP | 2205460 B1 | 3/2016 |
| FR | 2988654 A1 | 10/2013 |
| GB | 2512136 A | 9/2014 |
| JP | 2001269380 A | 10/2001 |
| JP | 2005137896 A | 6/2005 |
| JP | 2005237456 A | 9/2005 |
| JP | 2006014756 A | 1/2006 |
| JP | 3857869 B2 | 12/2006 |
| JP | 2009172145 A | 8/2009 |
| JP | 2012196253 A | 10/2012 |
| JP | 2013163405 A | 8/2013 |

(56) References Cited

FOREIGN PATENT DOCUMENTS

| | | |
|---|---|---|
| JP | 2019131049 A | 8/2019 |
| WO | 2011144280 A1 | 11/2011 |
| WO | 2012039368 | 3/2012 |
| WO | 2013144498 A1 | 10/2013 |
| WO | 2015127193 A1 | 8/2015 |

* cited by examiner

SEAT SYSTEM

TECHNICAL FIELD

The present disclosure generally relates to seat systems, including seat systems that may be used in connection with vehicles, such as automobiles.

BACKGROUND

This background description is set forth below for the purpose of providing context only. Therefore, any aspect of this background description, to the extent that it does not otherwise qualify as prior art, is neither expressly nor impliedly admitted as prior art against the instant disclosure.

Some seat systems may not be configured to monitor medical states of users/occupants. For example, some seat systems may not be configured to assess the medical state of injured occupants following a detected collision and/or prioritize users/occupants for emergency medical assistance.

There is a desire for solutions/options that minimize or eliminate one or more challenges or shortcomings of seat systems. The foregoing discussion is intended only to illustrate examples of the present field and is not a disavowal of scope.

SUMMARY

In embodiments, a seat system may include a seat, a sensor assembly, and/or an electronic control unit (ECU) connected with the sensor assembly. The sensor assembly may be configured to sense a breathing pattern of a user associated with the seat. The ECU may be configured to communicate with a remote server, and at least one of the ECU and the remote server may be configured to determine a medical state of said user according, at least in part, to the breathing pattern.

With embodiments, a vehicle seat system may include a seat assembly including a first seat and a second seat, a sensor assembly configured to obtain first breathing pattern information associated with a first user associated with the first seat and second breathing pattern information associated with a second user associated with the second seat, and/or an ECU connected with the sensor assembly. The ECU may be configured to communicate with a remote server. At least one of the ECU and the remote server may be configured to determine (i) a first medical state of said first user according, at least in part, to the first breathing pattern information, and (ii) a second medical state of said second user according, at least in part, to the second breathing pattern information.

In embodiments, a method of operating a seat system may include providing a sensor assembly connected with the seat and the ECU, sensing biomedical information of a user of the seat via the sensor assembly, determining a medical state of said user according, at least in part, to the biomedical information, and/or transmitting at least one of the biomedical information and the medical state to a remote server.

The foregoing and other potential aspects, features, details, utilities, and/or advantages of examples/embodiments of the present disclosure will be apparent from reading the following description, and from reviewing the accompanying drawings.

BRIEF DESCRIPTION OF THE DRAWINGS

While the claims are not limited to a specific illustration, an appreciation of various aspects may be gained through a discussion of various examples. The drawings are not necessarily to scale, and certain features may be exaggerated or hidden to better illustrate and explain an innovative aspect of an example. Further, the exemplary illustrations described herein are not exhaustive or otherwise limiting, and are not restricted to the precise form and configuration shown in the drawings or disclosed in the following detailed description. Exemplary illustrations are described in detail by referring to the drawings as follows:

DETAILED DESCRIPTION

Reference will now be made in detail to embodiments of the present disclosure, examples of which are described herein and illustrated in the accompanying drawings. While the present disclosure will be described in conjunction with embodiments and/or examples, it will be understood that they do not limit the present disclosure to these embodiments and/or examples. On the contrary, the present disclosure covers alternatives, modifications, and equivalents.

Figure 1:
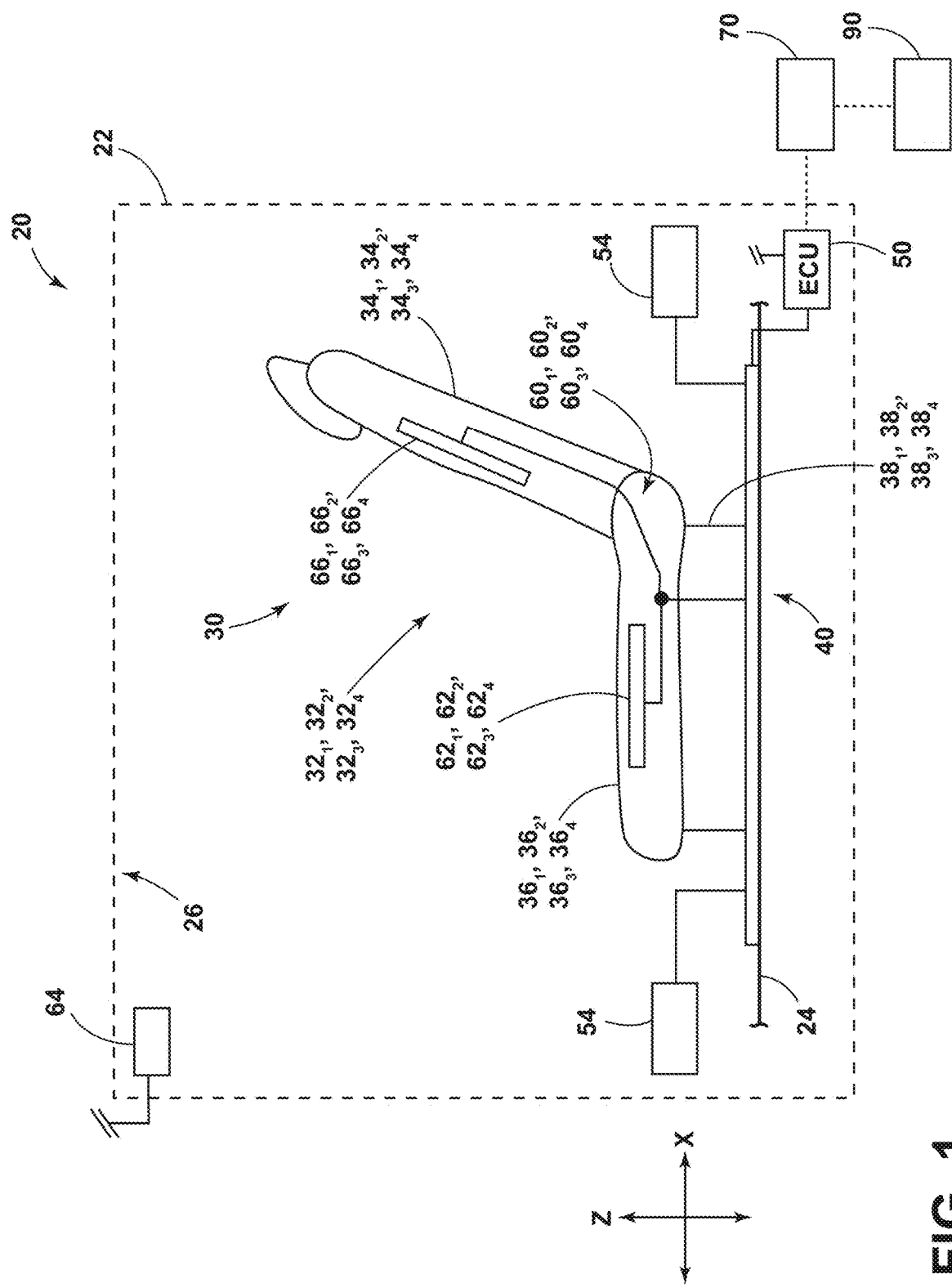
FIG. 1 is a side view generally illustrating an embodiment of a seat system according to teachings of the present disclosure.

In embodiments, such as generally illustrated in FIG. 1, a seat system 20 may include a seat assembly 30, a track assembly 40, and/or an electronic control unit (ECU) 50. The ECU 50 may be connected (e.g., electrically) with the seat assembly 30. The ECU 50 may be connected with one or more sensor assemblies $60_N$. The sensor assemblies $60_N$ may be disposed within, on, and/or proximate one or more seats $32_N$ of the seat assembly 30 such that the ECU 50 may be configured to identify the medical states of one or more users (e.g., occupants). The ECU 50 may be configured to determine a condition of a user and/or transmit information regarding the medical condition of the user. The seat system 20 may, for example and without limitation, be used in connection with a vehicle 22 and/or other modes of transportation.

Figure 2:
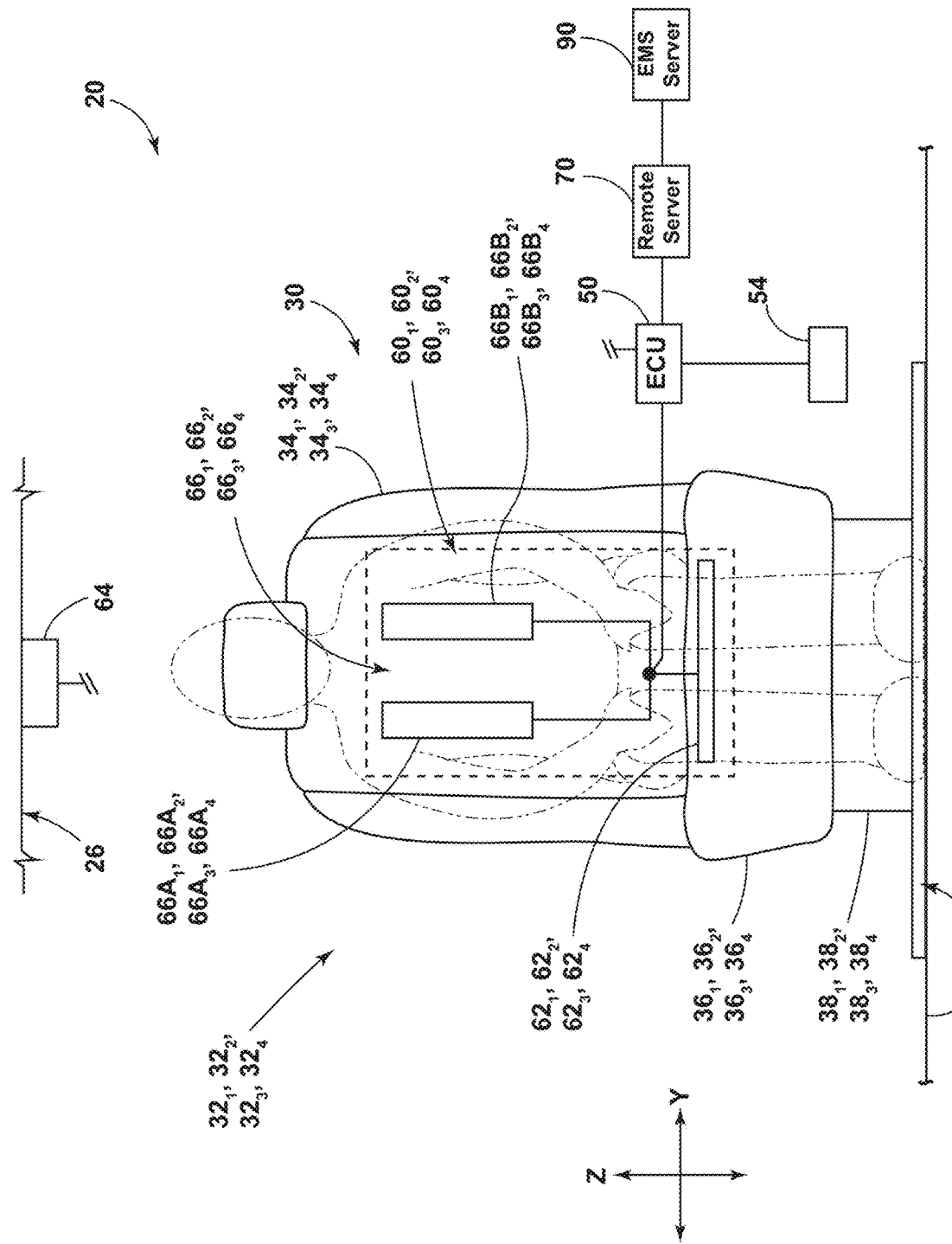
FIG. 2 is a front view generally illustrating an embodiment of a seat system according to teachings of the present disclosure.
Figure 3:
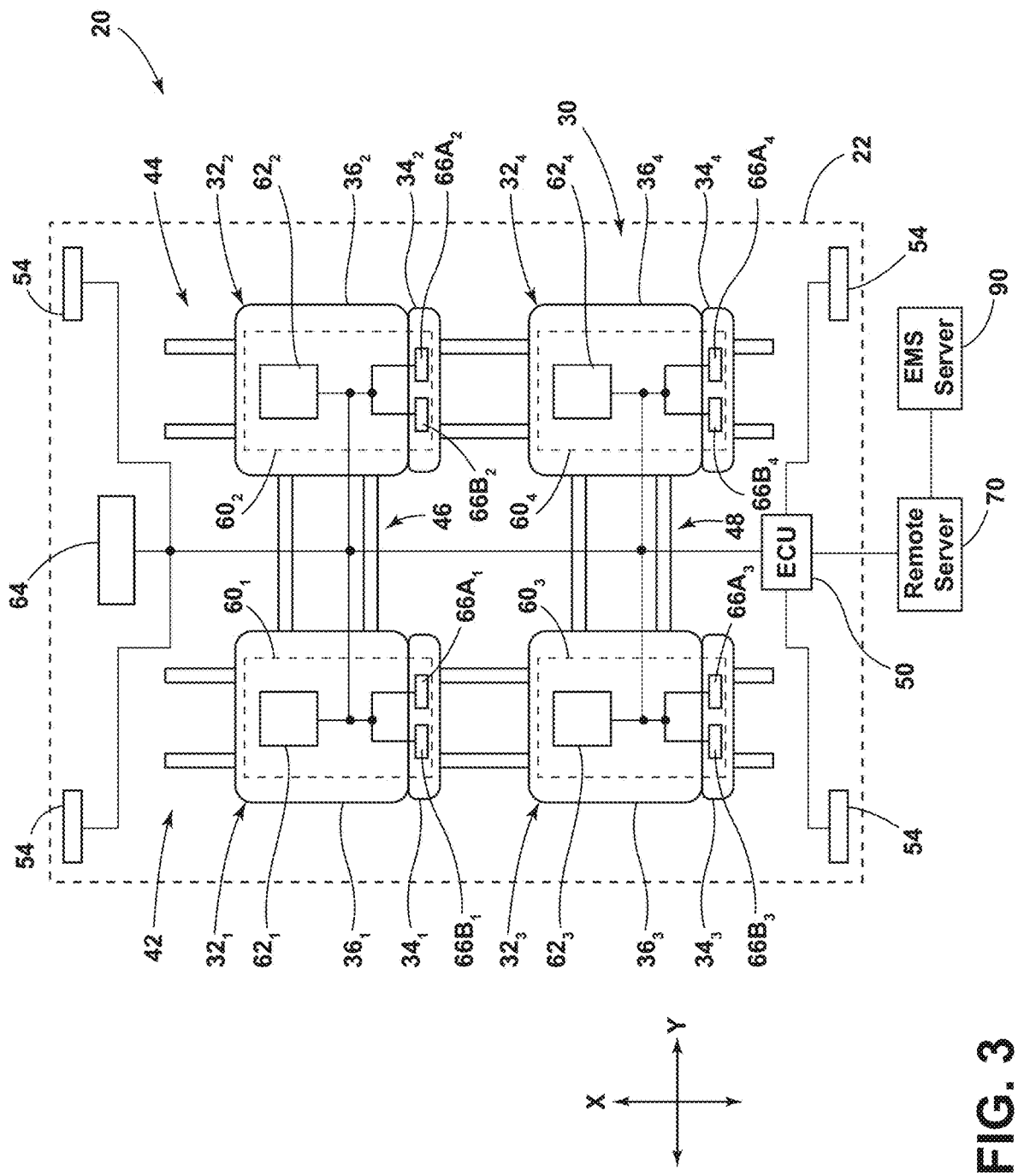
FIG. 3 is a top view generally illustrating an embodiment of a seat system according to teachings of the present disclosure.

In embodiments, such as generally illustrated in FIGS. 1, 2 and 3, a seat assembly 30 may be connected with a track assembly 40. The seat assembly 30 may include one or more seats $32_N$. For example and without limitation, the seat assembly 30 may include a first seat $32_1$, a second seat $32_2$, a third seat $32_3$, and/or a fourth seat $32_4$. The first seat $32_1$, the second seat $32_2$, the third seat $32_3$, and/or the fourth seat $32_4$ may include seat backs $34_1, 34_2, 34_3, 34_4$, and/or seat bases $36_1, 36_2, 36_3, 36_4$, respectively. The seats $32_N$ may be selectively connected (e.g., electrically and/or mechanically) to the track assembly 40. For example and without limitation, the seats 32N may be configured to be removed from the track assembly 40. The ECU 50 may be electrically connected to the seats $32_N$, such as via the track assembly

40. The ECU 50 may be configured to at least partially control operation of the first seat $32_1$, the second seat $32_2$, the third seat $32_3$, and/or the fourth seat $32_4$. The seats $32_N$ may be connected with the track assembly 40 via respective support members $38_N$ (e.g., support members $38_1$, $38_2$, $38_3$, $38_4$). The support members $38_N$ may be selectively connected with the track assembly 40. For example and without limitation, the support members $38_N$ may be configured to be inserted vertically and/or horizontally into the track assembly 40. The support members $38_N$ may be configured to be removed vertically and/or horizontally from the track assembly 40. The support members $38_N$ may be configured to move along the track assembly 40 (e.g., in the X-direction). For example and without limitation, the support members $38_N$ may be selectively locked in a plurality of positions along the track assembly 40.

With embodiments, such as generally illustrated in FIGS. 1, 2, and 3, a track assembly 40 may be disposed on a mounting surface 24 (e.g., a vehicle floor). The track assembly 40 may be configured to receive the seats $32_N$ substantially in the X-direction and/or the Z-direction. The seats $32_N$ and/or the support members $38_N$ may be configured to be selectively inserted into and/or selectively removed from the track assembly 40 in a plurality of locations along the track assembly 40. The track assembly 40 may, for example and without limitation, include one or more of a variety of shapes, sizes, and/or configurations, and/or may be configured such that seats $32_N$ may move in at least two directions with respect to the track assembly 40 (e.g., within a vehicle 22). The track assembly 40 may include one or more track portions 42, 44 that may be configured to facilitate movement of the seats $32_N$ in at least one direction. A first track portion 42 and/or a second track portion 44 may extend substantially parallel to each other and/or may extend generally in the X-direction. The seats $32_N$ may be selectively connected to the track assembly 40 via the support members $38_N$. For example and without limitation, the first seat $32_1$ and/or the third seat $32_3$ may be connected with the first track portion 42, and/or the second seat $32_2$ and/or the fourth seat $32_4$ may be connected with the second track portion 44.

In embodiments, such as generally illustrated in FIG. 3, the track assembly 40 may include a third track portion 46 and/or a fourth track portion 48 that may extend generally in the Y-direction (e.g., substantially perpendicular to the first track portion 42 and/or the second track portion 44). The seats $32_1$, $32_2$, $32_3$, $32_4$ may be configured to move between the first track portion 42 and/or the second track portion 44 via the third track portion 46 and/or the fourth track portion 48. The ECU 50 may be configured to move the seats $32_1$, $32_2$, $32_3$, $32_4$ along the first track portion 42, the second track portion 44, the third track portion 46, and/or the fourth track portion 48.

With embodiments, some or all of the track portions 42, 44, 46, 48 may include first and second sets of fixed and movable tracks. The fixed tracks may be fixed to the mounting surface 24. The movable tracks may be connected to support members $38_N$ and may be configured to move (e.g., slide) along the fixed tracks.

In embodiments, such as generally illustrated in FIGS. 1, 2, 3, and 4, the seat system 20 may include an ECU 50. For example and without limitation, the first seat $32_1$, the second seat $32_2$, the third seat $32_3$, and/or the fourth seat $32_4$ may be electrically connected with the ECU 50 (e.g., via a wired and/or wireless connection). The ECU 50 may be configured to control movement and/or positions of the first seat $32_1$, the second seat $32_2$, the third seat $32_3$, and/or the fourth seat $32_4$.

With embodiments, such as generally illustrated in FIGS. 1, 2, and 3, the seat system 20 may include and/or be connected to one or more vehicle sensors 54. The vehicle sensors 54 may, for example and without limitation, be configured to obtain crash information and/or detect a crash situation (e.g., if the vehicle 22 has experienced a collision). The vehicle sensors 54 may be connected with the ECU 50 such that the ECU 50 may receive information from the vehicle sensors 54 to determine whether a collision occurred. The vehicle sensors 54 may be sensors configured to measure a change in direction and/or sudden force (e.g., such as via force sensors, gyro-sensors, acceleration sensors, etc.). The vehicle sensors 54 may, for example, disposed in one or more of a variety of locations in and/or around a vehicle 22, such as at or about outer portions of a vehicle 22.

Figure 4:
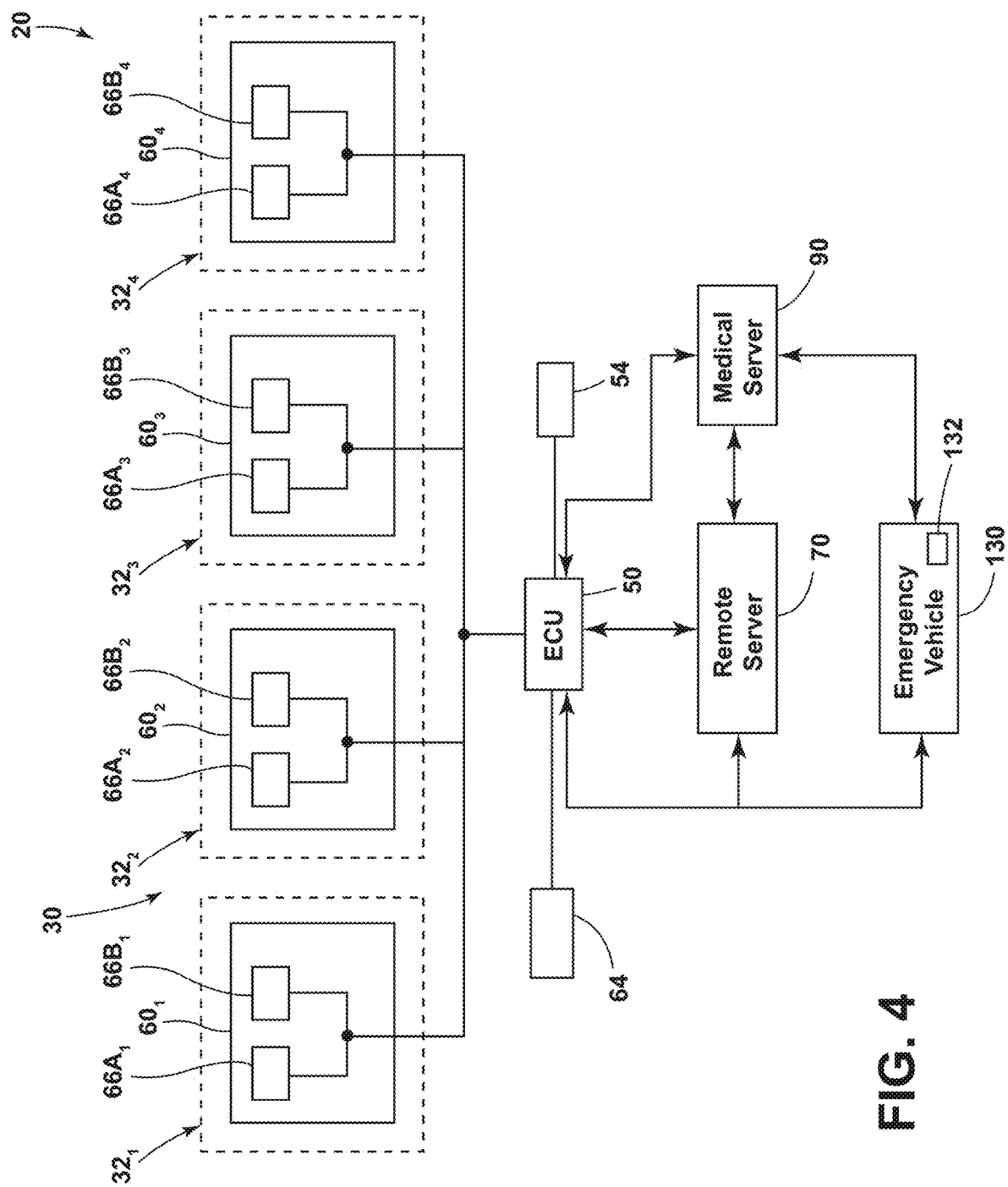
FIG. 4 is a schematic generally illustrating an embodiment of a seat system according to teachings of the present disclosure.

In embodiments, such as generally illustrated in FIGS. 2, 3, and 4, one or more seats $32_N$ of the seat system 20 may include and/or be connected to a respective sensor assembly $60_N$. For example and without limitation, the first seat $32_1$ may include a first sensor assembly $60_1$, the second seat $32_2$ may include a second sensor assembly $60_2$, the third seat $32_3$ may include a third sensor assembly $60_3$, and/or the fourth seat $32_4$ may include a fourth sensor assembly $60_4$. The sensor assemblies $60_N$ may include one or more of a variety of shapes, sizes, and/or configurations. The sensor assemblies $60_N$ may include one or more of a variety of different types of sensors, such as contact sensors and/or contactless sensors. For example and without limitation, the sensor assemblies $60_N$ may include, but are not limited to, occupancy sensors, pressure sensors, weight sensors, piezoelectric sensors, electrodermal sensors, photoplethysmographic sensors, seat bladders (e.g., fluid/air bladders), steering wheel sensors, biomedical sensors (e.g., configured to sense biomedical, biometric, and/or physiological information of a user), contact sensors, contactless sensors, cameras, vision devices, and/or radar sensors. The sensor assemblies $60_N$ may be electrically connected with the ECU 50 (e.g., via a wired and/or wireless connection). The ECU 50 may be configured to receive user/occupant information from the first sensor assembly $60_1$, the second sensor assembly $60_2$, the third sensor assembly $60_3$, and/or the fourth sensor assembly $60_4$ corresponding with the first seat $32_1$, the second seat $32_2$, the third seat $32_3$, and/or the fourth seat $32_4$, respectively. The ECU 50 may be configured to analyze and/or interpret the user/occupant information, and/or the ECU 50 may be configured to transmit the user/occupant information for analyzing and/or interpretation, such as to a remote server 70. A remote server 70 may, for example and without limitation, include a computing device disposed outside of a vehicle 22.

With embodiments, such as generally illustrated in FIGS. 2, 3, and 4, one or more sensor assemblies $60_N$ may include an occupancy sensor $62_N$. For example and without limitation, the first sensor assembly $60_1$ may include a first occupancy sensor $62_1$, the second sensor assembly $60_2$ may include a second occupancy sensor $62_2$, the third sensor assembly $60_3$ may include a third occupancy sensor $62_3$, and/or the fourth sensor assembly $60_4$ may include a fourth occupancy sensor $62_4$. The occupancy sensors $62_N$ may include one or more of a variety of sensors. For example and without limitation, the occupancy sensors $62_N$ may be a single sensor or any combination of sensors, such as pressure sensors, weight sensors, piezoelectric sensors, radar sensors, and/or proximity sensors. The occupancy sensors $62_N$ may be disposed proximate a surface of the seat backs $34_N$, and/or the seat bases $36_N$. The ECU 50 may receive occupancy information from the occupancy sensors $62_N$, and/or the ECU 50 may be configured to determine the occupancy of the first seat 32₁, the second seat 32₂, the third seat 32₃, and/or the fourth seat 32₄ via the sensor assemblies 60₁, 60₂, 60₃, 60₄ (e.g., from the occupancy information).

In embodiments, such as generally illustrated in FIGS. 1, 2, 3, and 4, the ECU 50 may be connected with a detection system 64, which may, for example, include a radar sensor/system, a Lidar sensor/system, and/or one or more cameras, among others. The detection system 64 may be disposed within the vehicle 22 such that one or more of seats $32_N$ are within a range or a field of view of the detection system 64 or component thereof. For example and without limitation, the detection system 64 may be disposed substantially towards a front of the vehicle 22 and/or substantially on a ceiling/roof 26 of a vehicle 22. The detection system 64 may be configured to obtain information about whether a seat $32_N$ is occupied, such as by an occupant and/or by cargo. The detection system 64 may be connected (e.g., wired and/or wirelessly) with the ECU 50, and/or may be configured to transmit information to the ECU 50 regarding the state of occupancy for the seats $32_N$. The ECU 50 may determine the occupancy of the seats $32_N$ based on the information from by the detection system 64. The ECU 50 and/or the detection system 64 may be configured for image processing and/or facial identification.

With embodiments, the ECU 50 and/or the detection system 64 may be configured to obtain reference occupancy information that may correspond to the seats $32_N$ being unoccupied, and may compare current information to the reference information to determine if a seat $32_N$ is occupied. Additionally or alternatively, the ECU 50 and/or the detection system 64 may be configured to determine whether a seat $32_N$ is occupied by an occupant or by cargo. For example and without limitation, if the ECU 50 and/or the detection system 64 determines that a seat $32_N$ is occupied and that whatever is occupying the seat $32_N$ is moving (e.g., fidgeting, talking, adjusting a seat belt, etc.), the ECU 50 and/or the detection system 64 may determine that the seat $32_N$ is occupied by an occupant and not just by cargo.

In embodiments, such as generally illustrated in FIGS. 1, 2, 3, and 4, one or more sensor assemblies $60_N$ may include a biomedical sensor $66_N$. For example and without limitation, the first sensor assembly 60₁ may include a first biomedical sensor 66₁, the second sensor assembly 60₂ may include a second biomedical sensor 66₂, the third sensor assembly 60₃ may include a third biomedical sensor 66₃, and/or the fourth sensor assembly 60₄ may include a fourth biomedical sensor 66₄. The biomedical sensors $66_N$ may be disposed at least partially within the seat backs $34_N$ and/or the seat bases $36_N$. The biomedical sensors $66_N$ may be disposed substantially proximate the user (e.g., a seat occupant) such as to increase the accuracy of the biomedical information sensed. The biomedical sensors $66_N$ may include one or more of a variety of sensors. For example and without limitation, the biomedical sensors $66_N$ may include sensors (e.g., piezoelectric sensors) configured to measure/read biomedical information (e.g., heart rate, breathing rate, blood pressure, fidget movements, etc.) of a user associated with (e.g., occupying, on, near, etc.) a seat $32_N$ of the seat assembly 30. The ECU 50 may be electrically connected (e.g., wired and/or wirelessly) with the biomedical sensors $66_N$, and/or may be configured to receive biomedical information from the biomedical sensors $66_N$. The ECU 50 may be configured to analyze, interpret, and/or transmit the biomedical information. For example and without limitation, the ECU 50 may be configured to assess the medical state of a user/occupant from the biomedical information, and/or to identify a user/occupant.

With embodiments, such as generally illustrated in FIGS. 2 and 3, a biomedical sensor $66_N$ may include a first sensor portion $66A_N$ (e.g., first sensor portions 66A₁, 66A₂, 66A₃, 66A₄) and/or a second sensor portion $66B_N$ (e.g., second sensor portions 66B₁, 66B₂, 66B₃, 66B₄). The first sensor portion $66A_N$ and/or the second sensor portion $66B_N$ may be disposed substantially within the seat backs $34_N$. The first sensor portion $66A_N$ and/or the second sensor portion $66B_N$ may be disposed substantially proximate an outer surface of the seat back $34_N$, such as to be sufficiently close to a user/occupant when or for collecting/reading/sensing information. The first sensor portion $66A_N$ and/or the second sensor portion $66B_N$ may extend substantially in a Z-direction and/or in a direction substantially parallel to the seat back $34_N$ (e.g., such as to align along a back of a user/occupant). Such as generally shown in FIG. 2, the first sensor portion $66A_N$ may be disposed substantially at a first side of the seat back $34_N$ (e.g., a left side), and/or the second sensor portion $66B_N$ may be disposed substantially on a second side of the seat back $34_N$ (e.g., a right side and/or opposite the first side). The first sensor portion $66A_N$ may be disposed to be substantially proximate a first lung of a user/occupant, and/or the second sensor portion $66B_N$ may be disposed to be substantially proximate a second lung of a user/occupant. The first sensor portion $66A_N$ and/or the second sensor portion $66B_N$ may be configured to monitor respiratory information of the first lung and/or the second lung, respectively. For example and without limitation, the first sensor portion $66A_N$ and/or the second sensor portion $66B_N$ may be configured to individually measure a breathing rate, respiratory pattern, and/or a variety of other respiration information for each corresponding lung.

In embodiments, the ECU 50 may be configured to monitor one or more physiological parameters of a user/occupant (e.g., heart rate, heart rate variability, fidgets, sneezing, drowsiness symptoms, diabetes, kidney function, etc.) via the biomedical sensors $66_N$. Movement of a user associated with breathing may impair monitoring physiological parameters (e.g., effectively act as noise), and the ECU 50 may filter out noise created by breathing motions to more accurately identify physiological parameters of a user (e.g., by removing/ignoring the measured breathing pattern of a user and/or motion detected by the detection system 64, such as via motion artifact correction). Additionally or alternatively, the ECU 50 may be configured to detect whether a user is speaking, which may alter the breathing pattern of the user, and the ECU 50 may be configured to compensate for such breathing pattern alterations (e.g., ignore/remove the alterations and/or estimates thereof).

With embodiments, such as generally illustrated in FIGS. 1, 2, 3, 4, and 5, the ECU 50 may be connected with a remote server 70. The ECU 50 may be configured to transmit information to the remote server 70 and/or receive information from the remote server 70. The remote server 70 may be configured to transmit information to the ECU 50 and/or receive information from the ECU 50. For example and without limitation, the remote server 70 may transmit a user profile to the ECU 50, which may be disposed within a vehicle 22. The user profile may include biometric profile information (e.g., for identifying a user) and/or medical/biomedical profile information (e.g., representing the medical history of the user). The ECU 50 and/or the remote server 70 may be configured to interpret/analyze the biometric profile information and/or the medical profile information. For example and without limitation, the remote server 70 may be connected one or more of a variety of additional devices/locations (e.g., servers, medical databases, emergency medical services, etc.) that may be capable of transmitting information and/or analyzing sensed information from the seat assembly 30.

In embodiments, the ECU 50 may receive biometric profile information and/or the ECU 50 may be configured to compare biometric profile information with sensed biometric/biomedical information to identify a user and the corresponding seat $32_N$. If the biometric profile information is substantially consistent with and/or similar to the sensed biometric/biomedical information, the ECU 50 may determine that the correct user is seated in the corresponding seat $32_N$. If the biometric profile information is not substantially consistent with and/or similar to the sensed biometric/biomedical information, the ECU 50 may determine that an incorrect user is seated in the respective seat $32_N$.

Figure 5:
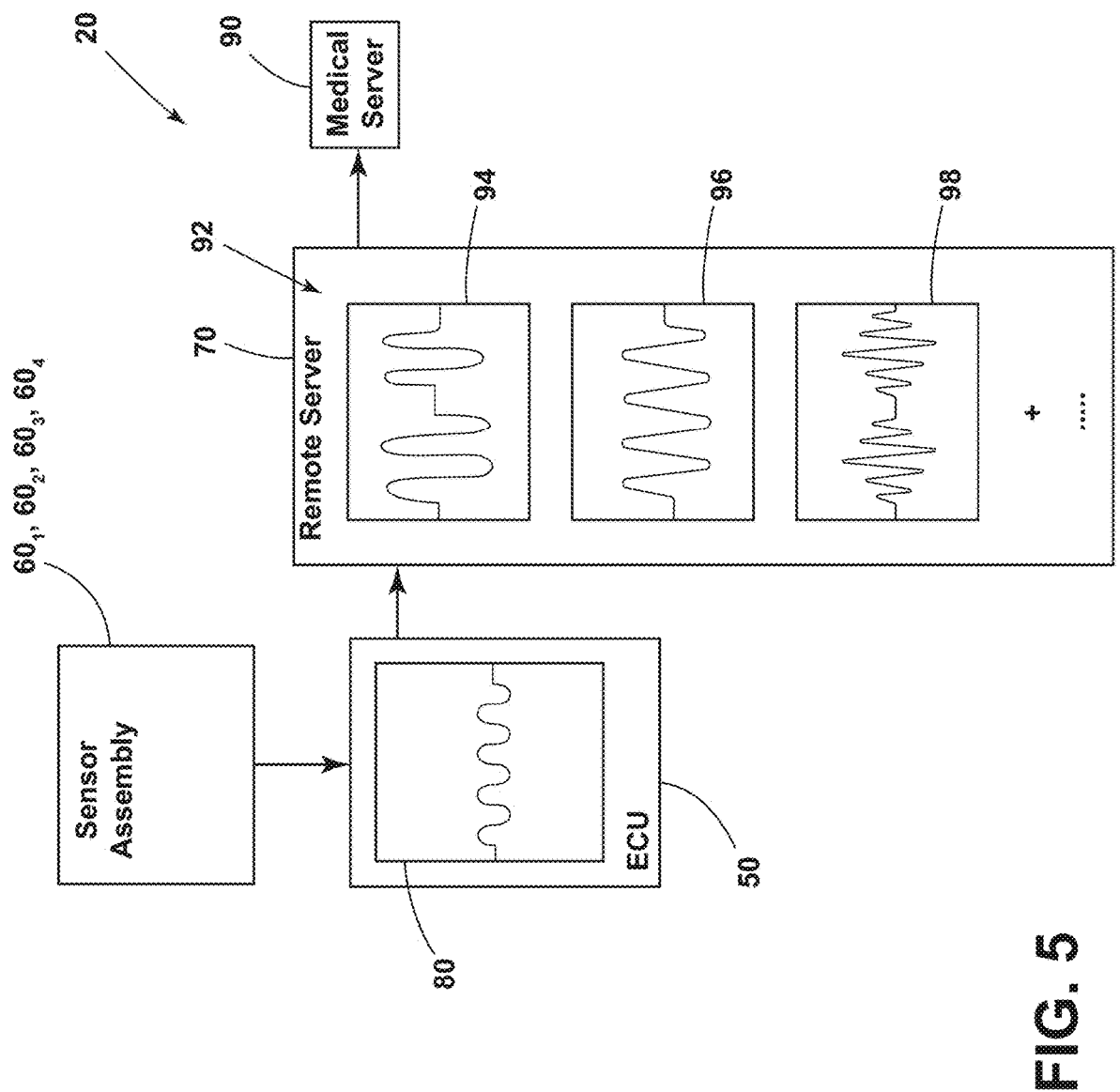
FIG. 5 is a schematic generally illustrating an embodiment of a seat system according to teachings of the present disclosure.
Figure 6:
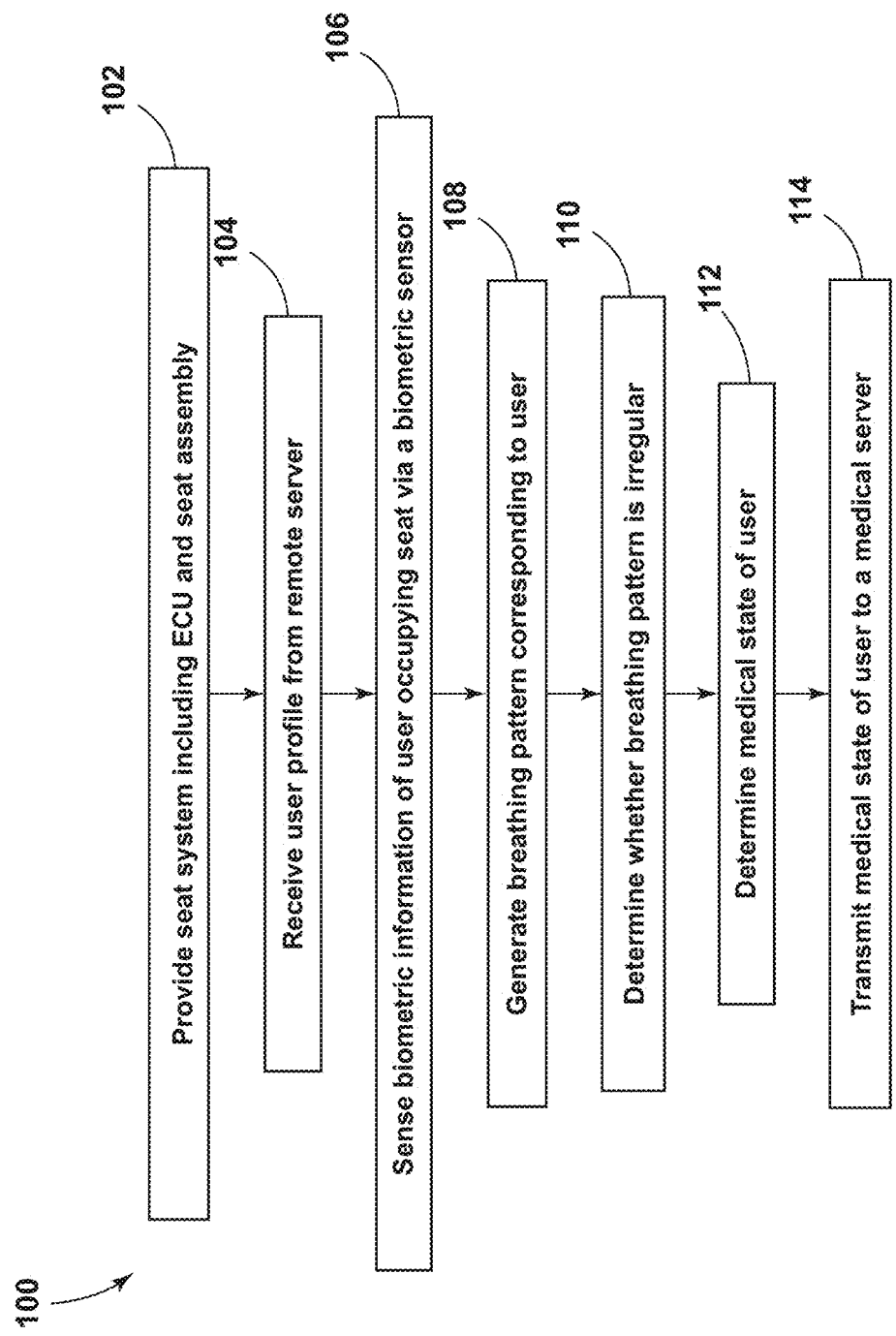
FIG. 6 is a flow-chart generally illustrating an embodiment of a method of operating a seat system according to teachings of the present disclosure.

In embodiments, such as generally illustrated in FIGS. 4 and 5, the ECU 50 may be configured to monitor a physical condition (e.g., a medical state) of a user occupying a seat $32_N$ of the seat assembly 30. The seat system 20 (e.g., the ECU 50) may be configured to sense a breathing pattern of a user via a sensor assembly $60_N$. The ECU 50 may be configured to generate a breathing pattern waveform 80 for one or more occupied seats $32_N$. The ECU 50 may receive sensed biomedical information from the sensor assemblies $60_N$, and/or the ECU 50 may plot/graph the sensed biomedical information into a breathing pattern waveform 80 to analyze the physical condition of a user. The ECU 50 may be configured to identify a user, receive information from the biomedical sensors $66_N$, generate a breathing pattern waveform 80 corresponding to the user, and/or store the biomedical information for transmission and/or analysis.

In embodiments, a remote server 70 may include and/or be connected to a medical server 90. While the remote server 70 and the medical server 90 are shown as separate for illustrative purposes in the embodiments of FIGS. 4 and 5, a remote server 70 and a medical server 90 may be incorporated together, at least in part, and/or may share one or more components (e.g., processors, memory, storage, etc.). The medical server 90 may include medical records and/or a medical database. The ECU 50 may transmit the breathing pattern waveform 80 to the remote server 70 (e.g., the medical server 90) such that the remote server 70 may compare the breathing pattern waveform 80 to information or data, for example one or more breathing pattern samples 92 stored in the remote server 70 (and/or a storage device connected thereto). For example and without limitation, the remote server 70 may be configured to access a variety of breathing pattern samples 92 (e.g., pathological respiration signatures) corresponding with a variety of respiratory medical conditions. The breathing pattern samples 92 may include, but are not be limited to, respiration waveforms associated with Biot's respiration (sample 94), Kussmaul breathing (sample 96), and/or Cheyne-Strokes respiration (sample 98), such as generally illustrated in FIG. 5.

With embodiments, a user profile and/or a remote server 70 may include biometric profile information corresponding to a typical/normal breathing pattern for a user. The ECU 50 and/or the remote server 70 may analyze the breathing pattern waveform 80 to assess the physical condition of the user. For example and without limitation, if (i) the ECU 50 and/or the remote server 70 matches the breathing pattern waveform 80 with a breathing pattern sample 94, 96, 98, and/or (ii) the breathing pattern waveform 80 is substantially different from the typical breathing pattern for a user (as indicated by the user profile), the ECU 50 and/or the remote server 70 may connect/transmit corresponding information (e.g., matching breathing pattern sample 92, 94, 96, breathing pattern abnormality, etc.) to one or more other devices, such as to a medical server 90, which may be associated with a medical and/or emergency services provider. The medical server 90 may conduct further analysis of the breathing pattern waveform 80, such as to assess and/or confirm a physical condition (e.g., a medical state) of one or more users of the seats $32_N$.

In embodiments, a typical/normal breathing pattern for a particular user may be an abnormal breathing pattern (e.g., somewhat-irregular breathing pattern) compared to an average user. The ECU 50 and/or the remote server 70 may use the abnormal breathing pattern as a baseline (e.g., the typical/normal pattern for the particular user) for comparison with the generated breathing pattern waveform 80.

In embodiments, an ECU 50 and/or a remote server 70 may determine whether a collision has occurred and/or may transmit crash information (e.g., as sensed by the vehicle sensors 54) to another location/device, such as to the remote server 70 and/or the medical server 90. The medical server 90 may utilize the crash information and the breathing pattern waveform 80 in assessing a physical condition/medical state of users. For example and without limitation, the ECU 50 and/or the remote server 70 may determine the direction/location of a vehicle collision and/or may prioritize the assessment of the seat(s) $32_N$ and the users therein substantially proximate the direction/location of the collision as users closer to the impact zone of the collision may require more immediate medical attention. Once the medical server 90 determines that a collision has occurred and/or that users are in need of medical attention, the medical server 90 may contact (e.g., dispatch) an emergency vehicle 130 (e.g., ambulance, fire truck, police car, etc.) to travel to the location of the vehicle 22.

With embodiments, an ECU 50, a remote server 70, and/or a medical server 90 may be configured to transmit user physical condition information to the emergency vehicle 130 and/or the operators thereof, such as via an electronic device 132 that may be associated with the emergency vehicle 130 and/or the operators. For example and without limitation, the user physical condition information may indicate a priority of assistance for the users of the vehicle 22. The medical server 90 may analyze the breathing pattern waveform 80 for each user and/or the medical server 90 may determine which users need medical assistance more urgently than other users within the vehicle 22. Determining the urgency for medical assistance may include evaluating pre-existing medical conditions and/or prior injuries, which may increase the urgency for medical assistance (e.g., high blood pressure, use of blood thinners, impaired immune system, etc.) or decrease the urgency for medical assistance (e.g., if a detected issue existed before the collision and was already being treated). Urgency information may be included in the user physical condition information, which may be provided to the emergency vehicle 130, and/or the user physical condition information may include a recommended priority of assistance for the users of the vehicle 22. Upon an emergency vehicle 130 arriving at the vehicle 22 after a collision, emergency vehicle operators/medical professionals may, for example and without limitation, assist users in the priority order as indicated by the user physical condition information. Medical personnel may consider the user physical condition information when preparing for and/or while assisting users.

With embodiments, an ECU 50, a remote server 70, and/or a medical server 90 may determine whether any users have been ejected from a respective seat $32_N$, such as a result of a collision, or if any users have exited the vehicle 22 (e.g., via the occupancy sensors $62_N$). For example and without limitation, the ECU 50 may determine which seats $32_N$ were occupied (e.g., by a living being) prior to the collision and which seats 32N are unoccupied after the collision (e.g., immediately after, before users may deliberately exit the seats $32_N$). If any seats $32_N$ that were occupied prior to the collision are unoccupied after the collision, the ECU 50 may provide an indication that a user and/or a number of users may have been ejected from a seat $32_N$ and/or a vehicle 22, such as to a remote server 70 and/or a medical server 90. The ECU 50 may be configured to exclude seats $32_N$ that are unoccupied after the collision if a restraint system of the seat $32_N$ has been deactivated by a user (e.g., if a vehicle sensor 54 and/or the sensor assembly 60 detects that a user unbuckled a seat belt).

In embodiments, a medical server 90 may combine the information from one or more vehicle sensors 54 (e.g., accelerometer, speedometer, compass, GPS, etc.) and one or more occupancy sensors $62_N$ to determine an expected location for a user that may have been ejected from the vehicle 22 as a result of the collision. For example and without limitation, the ECU 50 may provide a vehicle speed and/or deceleration at the time of the collision to the medical server 90, which may estimate a potential distance from the vehicle 22 that a user may be according, at least in part, to the speed/deceleration.

With embodiments, an ECU 50, a remote server 70, and/or a medical server 90 may be configured to obtain an authorization from a user to share health/medical information with appropriate third parties (e.g., medical professionals), such as to comply with Health Insurance Portability and Accountability Act (HIPAA) regulations. An ECU 50, a remote server 70, and/or a medical server 90 may not communicate any health or medical information about a user unless such an authorization has been obtained.

In embodiments, a method 100 of operating a seat system 20 may include providing a seat system 20, which may include an ECU 50 and a seat assembly 30 having one or more seats $32_N$ (step 102). The method 100 may include the ECU 50 receiving a user profile from a remote server 70 (step 104). The user profile may include one or more of a variety of types of information. For example and without limitation, the user profile may include a typical breathing pattern of a user, a seat assignment, prior/current medical conditions, and/or biometric information. The method 100 may include sensing (e.g., via one or more biomedical sensors $66_N$, and/or one or more occupancy sensors $62_N$) biometric/biomedical information of a user occupying a seat 32, which may be used by the ECU 50 for identifying and/or confirming the identity of the user (step 106). The method 100 may include generating a breathing pattern waveform 80 for users seated in respective seats $32_N$ of the seat system (step 108). The method 100 may include the ECU 50 comparing the breathing pattern waveform 80 with information from the corresponding user profile. The ECU 50 may determine whether the breathing pattern waveform 80 is substantially similar to the information from the user profile (e.g., an expected breathing pattern waveform for the user). If the breathing pattern waveform 80 is substantially similar to/consistent with the biomedical information, the ECU 50 may not take further diagnostic action. However, if the breathing pattern waveform 80 is materially different than the biomedical information from the user profile, the ECU 50 may transmit the information to a remote server 70 (step 110).

With embodiments, the remote server 70 may include a medical server 90 and/or medical database. The method 100 may include the remote server 70 determining a physical condition/medical state of a user (step 112), which may include analyzing the breathing pattern waveform 80. Analyzing a breathing pattern waveform 80 may include comparing the breathing pattern waveform 80 with a variety of waveforms corresponding to medical conditions. If the remote server 70 determines that a user requires medical assistance, the remote server 70 may transmit user physical condition information to a medical server 90 (e.g., a medical assistance provider) (step 114). The physical condition information may a priority order for the users of a seat system 20. Medical personnel associated with the emergency service may use the user physical status information, which may include the priority order, to determine the order in which to provide medical assistance to the users. Users with more traumatic/urgent conditions may be treated before other users according to the determined priority order.

In embodiments, one or more portions of a method of operating a seat system 20 (e.g., method 100) may be conducted while a vehicle 22 is in motion and/or when a vehicle 22 is stopped.

In embodiments, one or more activities that may be conducted by an ECU 50, a remote server 70, and/or a medical server 90 may, additionally or alternatively, be conducted by another one of the ECU 50, the remote server 70, and/or the medical server 90.

In examples, a computing device (e.g., ECU 50, remote server 70, medical server 90) may include an electronic controller and/or include an electronic processor, such as a programmable microprocessor and/or microcontroller. In embodiments, a computing device may include, for example, an application specific integrated circuit (ASIC). A computing device may include a central processing unit (CPU), a memory (e.g., a non-transitory computer-readable storage medium), and/or an input/output (I/O) interface. A computing device may be configured to perform various functions, including those described in greater detail herein, with appropriate programming instructions and/or code embodied in software, hardware, and/or other medium. In embodiments, a computing device may include a plurality of controllers. In embodiments, a computing device may be connected to a display, such as a touchscreen display.

Various examples/embodiments are described herein for various apparatuses, systems, and/or methods. Numerous specific details are set forth to provide a thorough understanding of the overall structure, function, manufacture, and use of the examples/embodiments as described in the specification and illustrated in the accompanying drawings. It will be understood by those skilled in the art, however, that the examples/embodiments may be practiced without such specific details. In other instances, well-known operations, components, and elements have not been described in detail so as not to obscure the examples/embodiments described in the specification. Those of ordinary skill in the art will understand that the examples/embodiments described and illustrated herein are non-limiting examples, and thus it can be appreciated that the specific structural and functional details disclosed herein may be representative and do not necessarily limit the scope of the embodiments.

Reference throughout the specification to "examples, "in examples," "with examples," "various embodiments," "with embodiments," "in embodiments," or "an embodiment," or the like, means that a particular feature, structure, or characteristic described in connection with the example/embodiment is included in at least one embodiment. Thus, appearances of the phrases "examples, "in examples," "with examples," "in various embodiments," "with embodiments," "in embodiments," or "an embodiment," or the like, in places throughout the specification are not necessarily all referring to the same embodiment. Furthermore, the particular features, structures, or characteristics may be combined in any suitable manner in one or more examples/embodiments. Thus, the particular features, structures, or characteristics illustrated or described in connection with one embodiment/example may be combined, in whole or in part, with the features, structures, functions, and/or characteristics of one or more other embodiments/examples without limitation given that such combination is not illogical or non-functional. Moreover, many modifications may be made to adapt a particular situation or material to the teachings of the present disclosure without departing from the scope thereof.

It should be understood that references to a single element are not necessarily so limited and may include one or more of such element. Any directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of examples/embodiments.

Joinder references (e.g., attached, coupled, connected, and the like) are to be construed broadly and may include intermediate members between a connection of elements and relative movement between elements. As such, joinder references do not necessarily imply that two elements are directly connected/coupled and in fixed relation to each other. The use of "e.g." in the specification is to be construed broadly and is used to provide non-limiting examples of embodiments of the disclosure, and the disclosure is not limited to such examples. Uses of "and" and "or" are to be construed broadly (e.g., to be treated as "and/or"). For example and without limitation, uses of "and" do not necessarily require all elements or features listed, and uses of "or" are inclusive unless such a construction would be illogical.

While processes, systems, and methods may be described herein in connection with one or more steps in a particular sequence, it should be understood that such methods may be practiced with the steps in a different order, with certain steps performed simultaneously, with additional steps, and/or with certain described steps omitted.

All matter contained in the above description or shown in the accompanying drawings shall be interpreted as illustrative only and not limiting. Changes in detail or structure may be made without departing from the present disclosure.

It should be understood that a computing device (e.g., ECU 50, remote server 70, medical server 90), a system, and/or a processor as described herein may include a conventional processing apparatus known in the art, which may be capable of executing preprogrammed instructions stored in an associated memory, all performing in accordance with the functionality described herein. To the extent that the methods described herein are embodied in software, the resulting software can be stored in an associated memory and can also constitute means for performing such methods. Such a system or processor may further be of the type having ROM, RAM, RAM and ROM, and/or a combination of non-volatile and volatile memory so that any software may be stored and yet allow storage and processing of dynamically produced data and/or signals.

It should be further understood that an article of manufacture in accordance with this disclosure may include a non-transitory computer-readable storage medium having a computer program encoded thereon for implementing logic and other functionality described herein. The computer program may include code to perform one or more of the methods disclosed herein. Such embodiments may be configured to execute via one or more processors, such as multiple processors that are integrated into a single system or are distributed over and connected together through a communications network, and the communications network may be wired and/or wireless. Code for implementing one or more of the features described in connection with one or more embodiments may, when executed by a processor, cause a plurality of transistors to change from a first state to a second state. A specific pattern of change (e.g., which transistors change state and which transistors do not), may be dictated, at least partially, by the logic and/or code.

What is claimed is:

1. A seat system, comprising
a seat;
a sensor assembly; and
an electronic control unit (ECU) connected with the sensor assembly;
wherein the sensor assembly is configured to sense a breathing pattern of a user associated with the seat;
the ECU is configured to communicate with a remote server;
at least one of the ECU and the remote server is configured to determine a medical state of said user according, at least in part, to the breathing pattern;
the sensor assembly includes a fluid bladder disposed to align, at least in part, with a lung of said user; and
the ECU is configured to detect whether said user is speaking and compensate for breathing pattern alterations corresponding to speaking.

2. The seat system of claim 1, wherein the sensor assembly includes an occupancy sensor; and
the ECU is configured to obtain an occupancy status of the seat via the occupancy sensor.

3. The seat system of claim 1, wherein the sensor assembly includes a biomedical sensor;
the biomedical sensor includes a piezoelectric sensor and/or a radar sensor; and
the ECU is configured to sense the breathing pattern of said user via the biomedical sensor.

4. The seat system of claim 1, wherein the sensor assembly includes a camera or vision device.

5. The seat system of claim 1, wherein the ECU is configured to generate a breathing pattern waveform associated with the breathing pattern of said user.

6. The seat system of claim 5, wherein the remote server is connected with a medical database;
the medical database includes sample breathing patterns; and
at least one of the ECU and the remote server is configured to compare the breathing pattern waveform with the sample breathing patterns.

7. The seat system of claim 1, wherein the remote server is configured to connect with a medical server; and
the remote server is configured to transmit the medical state of said user to the medical server
at least one of the remote server and the medical server is configured to transmit the medical state to an emergency vehicle.

8. A vehicle seat system, comprising:
a seat assembly including a first seat and a second seat;

a sensor assembly configured to obtain first breathing pattern information associated with a first user associated with the first seat and second breathing pattern information associated with a second user associated with the second seat; and an ECU connected with the sensor assembly;

wherein the ECU is configured to communicate with a remote server;

at least one of the ECU and the remote server is configured to determine (i) a first medical state of said first user according, at least in part, to the first breathing pattern information, and (ii) a second medical state of said second user according, at least in part, to the second breathing pattern information; and at least one of the ECU and said remote server is configured to determine a medical priority order of said first user and said second user according to the first medical state and the second medical state.

9. The vehicle seat system of claim 8, wherein the sensor assembly includes a biomedical sensor connected to the first seat;

the biomedical sensor includes a first portion and a second portion;

the first portion is configured to sense first lung information corresponding to a first lung of said first user; and the second portion is separate from the first portion and is configured to sense second lung information corresponding to a second lung of said first user.

10. The vehicle seat system of claim 8, wherein at least one of the ECU and said remote server is configured to determine whether any users have been ejected from the seat assembly.

11. The vehicle seat system of claim 8, wherein determining the medical priority order includes evaluating pre-existing medical conditions of the first user and the second user.

12. The vehicle seat system of claim 8, wherein said remote server is configured to transmit the medical priority order, the first breathing pattern information, and the second breathing pattern information to an electronic device associated with an emergency vehicle and/or a medical services professional to facilitate treatment of at least one of said first user and said second user.

13. A method of operating a seat system including an ECU and a seat assembly having a seat, the method comprising:
providing a sensor assembly connected with the seat and the ECU;

sensing biomedical information of a user of the seat via the sensor assembly;

determining a medical state of said user according, at least in part, to the biomedical information;

transmitting at least one of the biomedical information and the medical state to a remote server;

sensing, via an additional sensor connected to an additional seat, additional biomedical information of an additional user associated with the additional seat; and determining a medical priority order of the said user and said additional user according to the biomedical information and the additional biomedical information.

14. The method of claim 13, wherein sensing biomedical information includes generating a breathing pattern waveform corresponding to said user.

15. The method of claim 14, including receiving a user profile associated with said user from the remote server, the user profile including biomedical information corresponding with said user; and comparing the breathing pattern waveform with the biomedical information of the user profile to determine whether the user requires medical attention.

16. The method of claim 14, wherein determining the medical state of said user includes comparing the breathing pattern waveform with a medical database connected with the remote server.

17. The method of claim 13, wherein the sensor assembly includes a biomedical sensor having a first portion and a second portion;

sensing biomedical information includes the first portion sensing a first lung of said user;
and sensing biomedical information includes the second portion sensing a second lung of said user.

18. The method of claim 13, wherein the sensor assembly includes a fluid bladder aligned, at least in part, with a lung of said user.

19. The method of claim 13, including transmitting the medical priority order to an electronic device associated with an emergency vehicle and/or a medical services professional.

20. The vehicle seat system of claim 8, wherein the ECU is configured to detect whether said first user is speaking and compensate for breathing pattern alterations corresponding to speaking.

* * * * *